United States Patent
Oku et al.

(10) Patent No.: US 8,976,347 B2
(45) Date of Patent: Mar. 10, 2015

(54) INSPECTION APPARATUS

(75) Inventors: Mizuki Oku, Tokyo (JP); Kei Shimura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/236,888

(22) PCT Filed: Aug. 3, 2012

(86) PCT No.: PCT/JP2012/069787
§ 371 (c)(1),
(2), (4) Date: Feb. 3, 2014

(87) PCT Pub. No.: WO2013/018878
PCT Pub. Date: Feb. 7, 2013

(65) Prior Publication Data
US 2014/0160470 A1 Jun. 12, 2014

(30) Foreign Application Priority Data
Aug. 3, 2011 (JP) ................................ 2011-169731

(51) Int. Cl.
*G01N 21/00* (2006.01)
*G01N 21/95* (2006.01)
*G01N 21/88* (2006.01)

(52) U.S. Cl.
CPC ........ *G01N 21/9501* (2013.01); *G01N 21/8806* (2013.01)
USPC .................... 356/237.2; 356/237.1; 356/237.5

(58) Field of Classification Search
CPC . G01N 21/9501; G01N 21/956; G01N 21/94; G01N 21/47
USPC .......................................... 356/237.1–237.5
See application file for complete search history.

(56) References Cited

U.S. PATENT DOCUMENTS 6,356,574 B1 * 3/2002 Craig et al. ...................... 372/75
7,271,890 B2 * 9/2007 Kim et al. ................... 356/237.2
(Continued)

FOREIGN PATENT DOCUMENTS

JP   11-251663 A   9/1999
JP   2001-108638 A   4/2001
(Continued)

OTHER PUBLICATIONS

International Search Report issued in International Application No. PCT/JP2012/069787 issued on Sep. 18, 2012.
(Continued)

*Primary Examiner* — Kara E Geisel
*Assistant Examiner* — Iyabo S Alli
(74) *Attorney, Agent, or Firm* — McDermott Will & Emery LLP

(57) ABSTRACT

Light that is scattered by a defect on a wafer is very weak, and a PMT and an MPPC are used as detection methods for measuring the weak light with high speed and sensitivity. The methods have a function of photoelectronically converting the weak light and multiplying an electron, but have a problem in that a signal light is lost and an S/N ratio is reduced because the quantum efficiency of the photoelectron conversion is as low as 50% or less. Direct light is amplified prior to the photoelectron conversion. The optical amplification is an amplification method in which the signal light and light of pump light are introduced into a rare-earth doped fiber, a stimulated emission is caused, and the signal light is amplified. In the present invention, the optical amplification is used. The amplification factor is changed according to various conditions.

8 Claims, 11 Drawing Sheets

(56) References Cited

U.S. PATENT DOCUMENTS

| | | |
|---|---|---|
| 2008/0068593 A1 | 3/2008 | Nakano et al. |
| 2009/0066940 A1 | 3/2009 | Matsui |
| 2009/0122305 A1 | 5/2009 | Makuuchi et al. |
| 2010/0210952 A1 | 8/2010 | Taira et al. |

FOREIGN PATENT DOCUMENTS

| | | | |
|---|---|---|---|
| JP | 2005-003447 A | 1/2005 |
| JP | 2008-096430 A | 4/2008 |
| JP | 2009-068903 A | 4/2009 |
| JP | 2009-115753 A | 5/2009 |
| JP | 2010-099095 A | 5/2010 |

OTHER PUBLICATIONS

English translation Notification of Reasons for Refusal Japanese Patent Application No. 2011-169731 dated Oct. 7, 2014.

* cited by examiner

[FIG. 1]
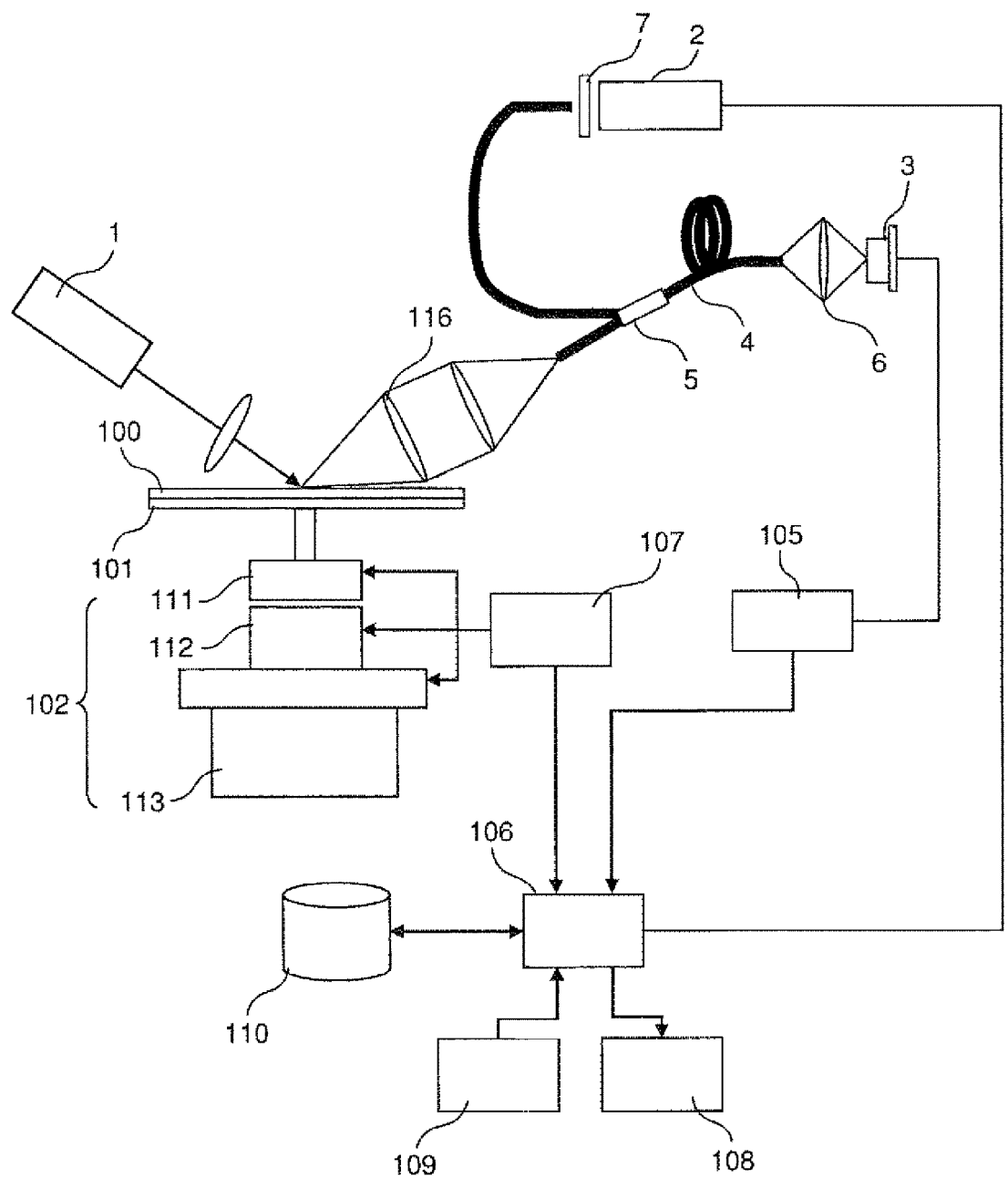

[FIG. 2]
(a)
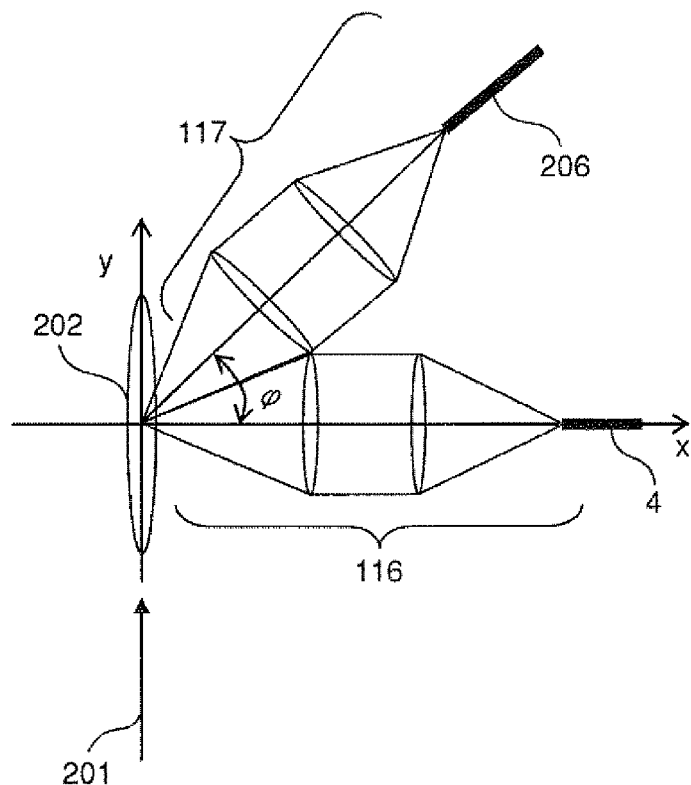
(b)
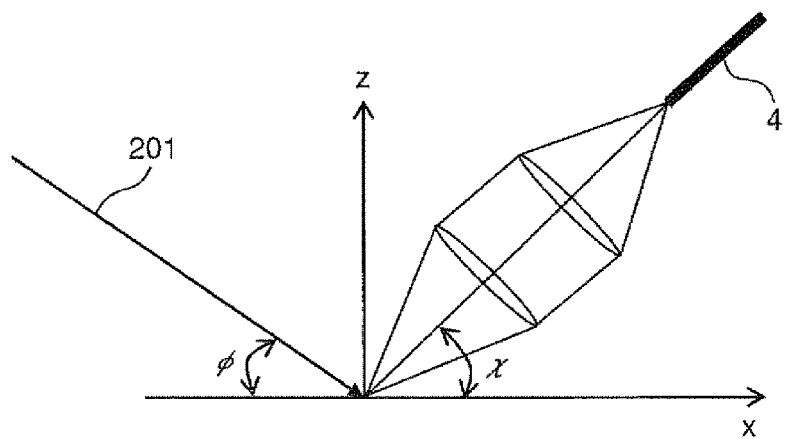

[FIG. 3]
(a)
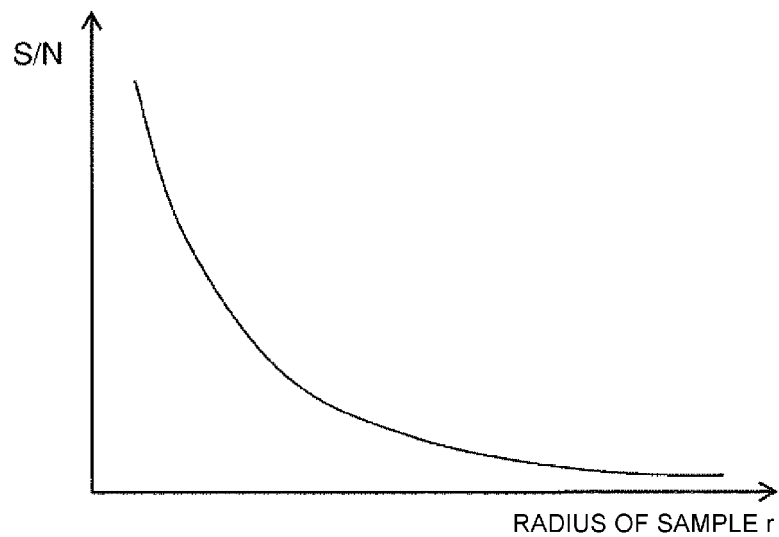
(b)
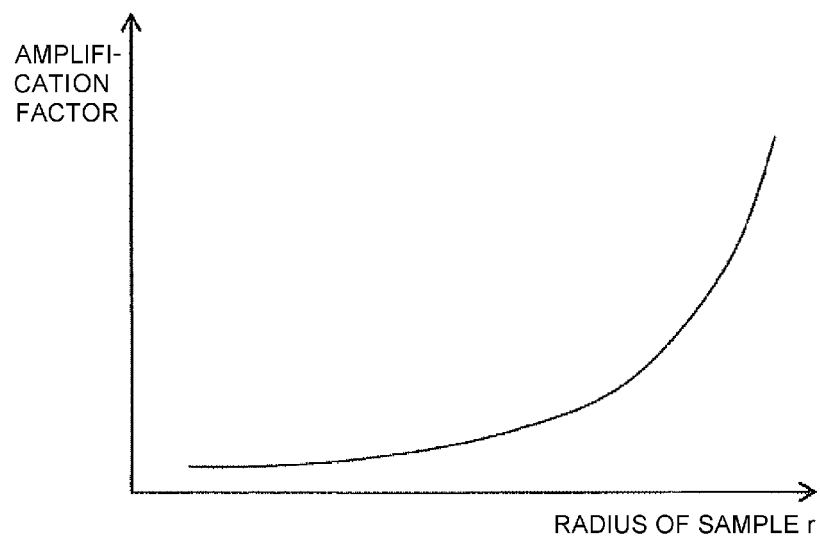

[FIG. 4]
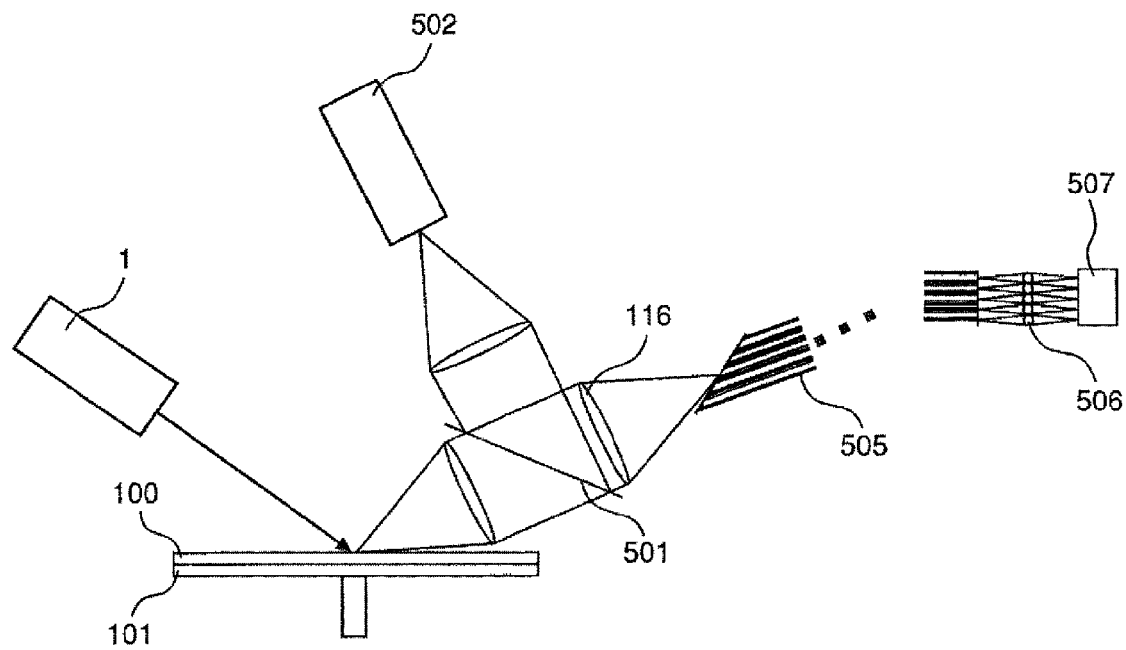

[FIG. 5]
(a)
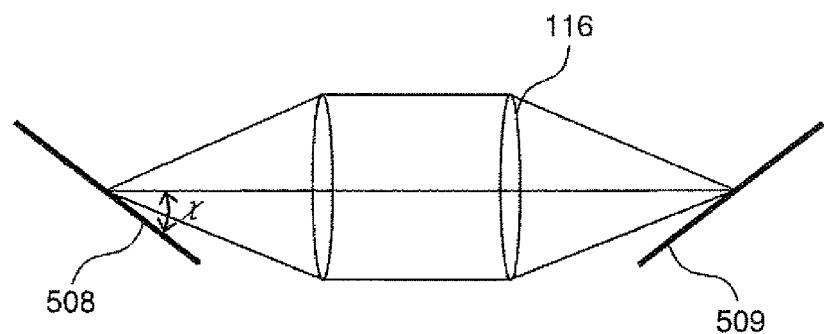
(b)
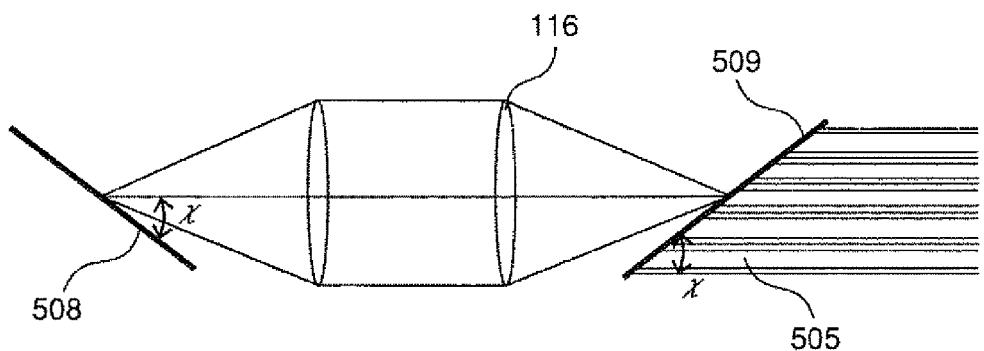
(c)
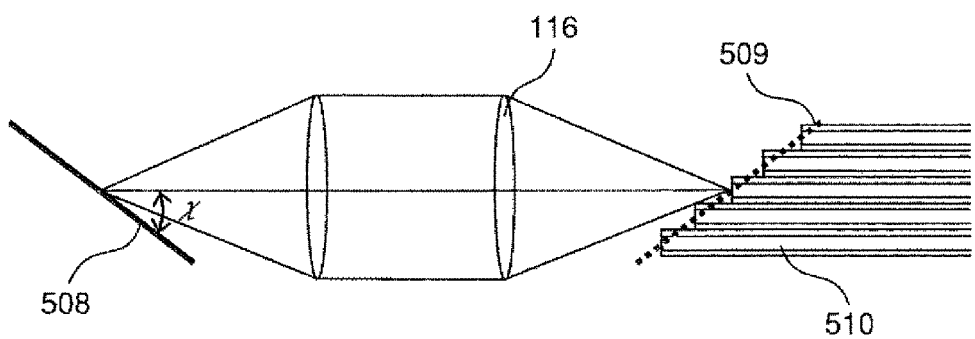

[FIG. 6]
(a)
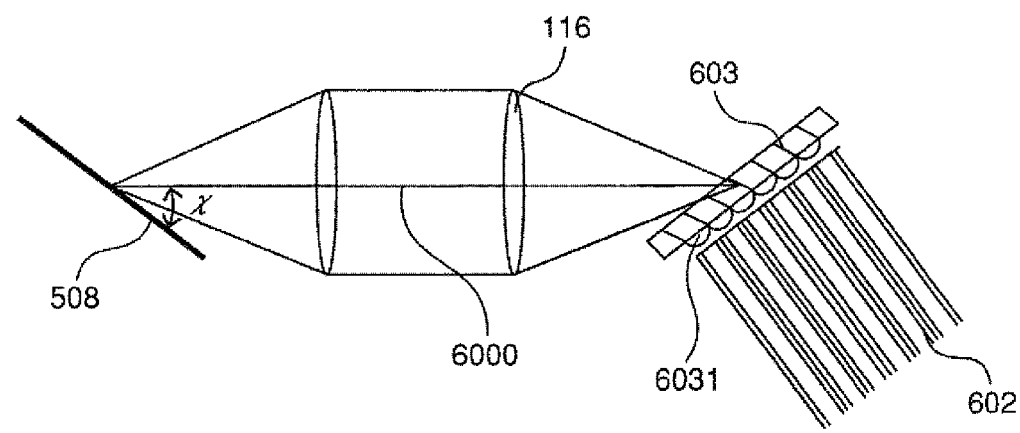
(b)
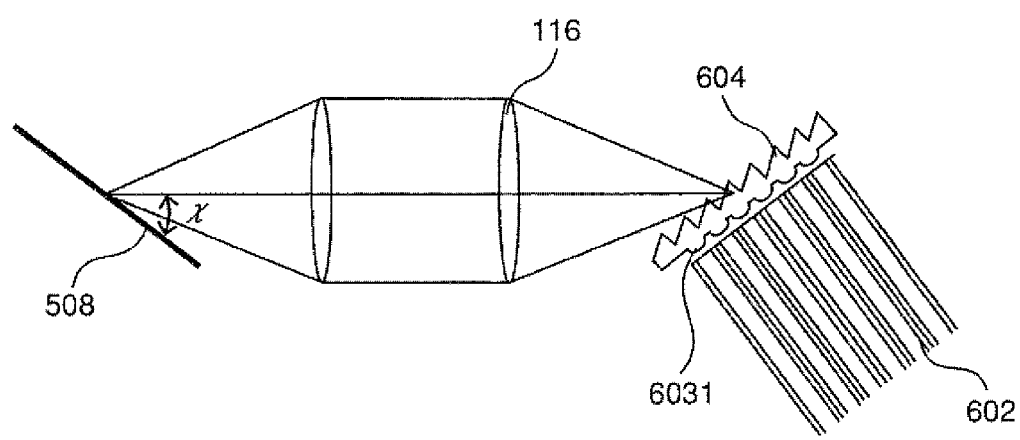

[FIG. 7]
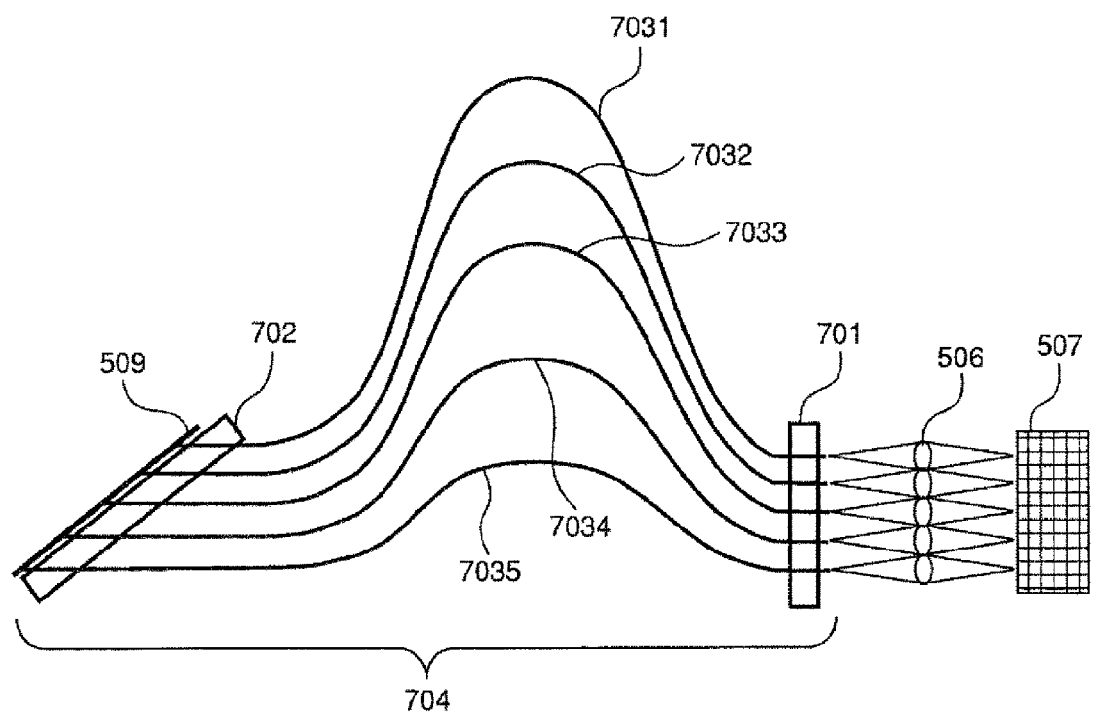

[FIG. 8]
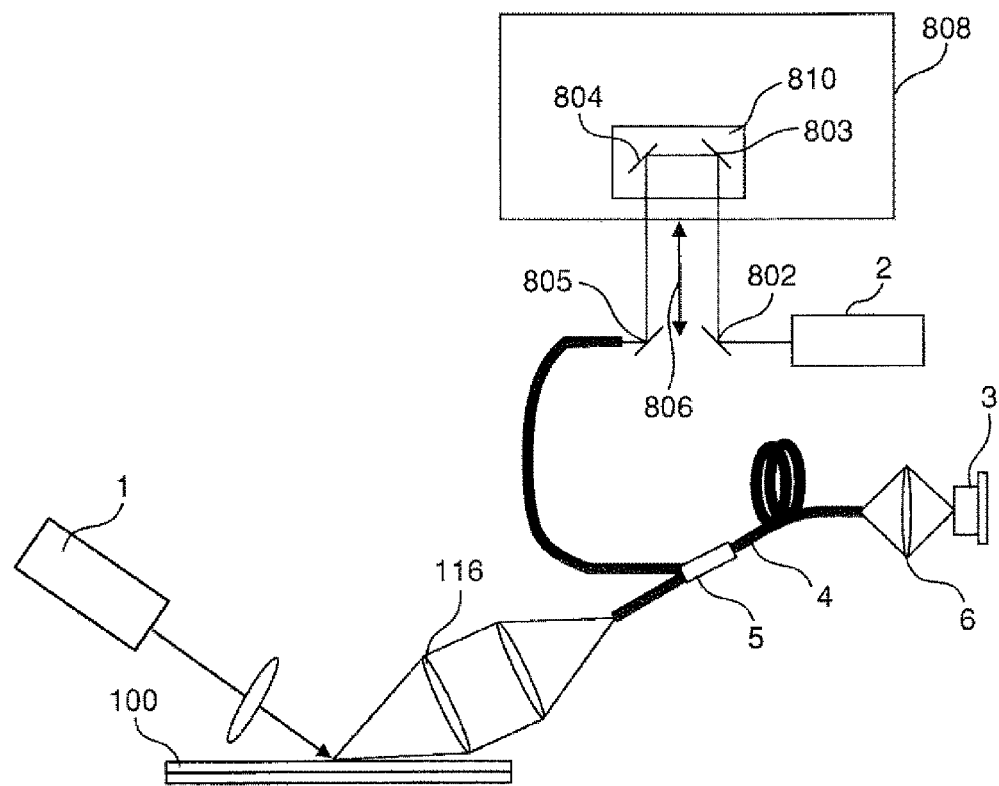
[FIG. 9]
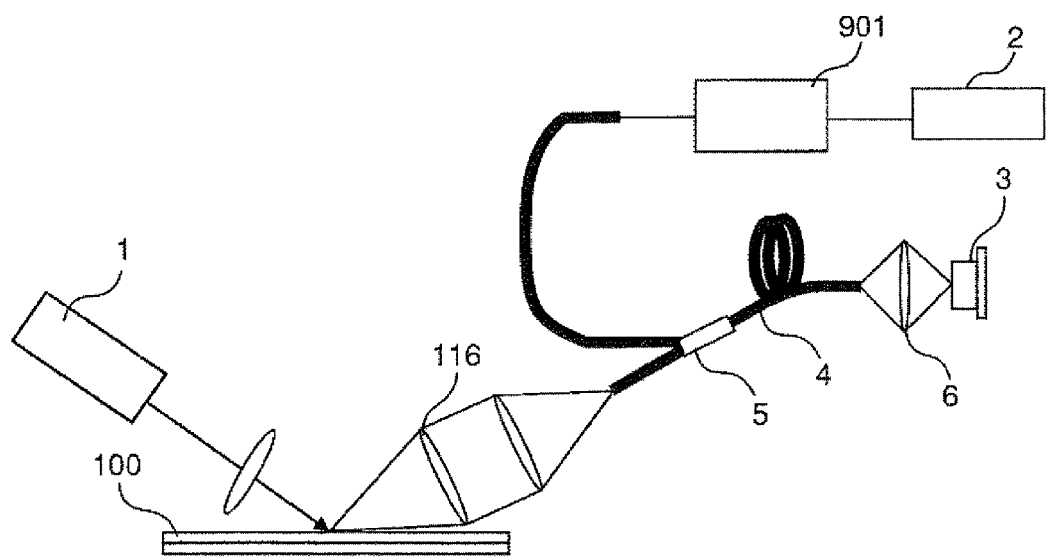

[FIG. 10]
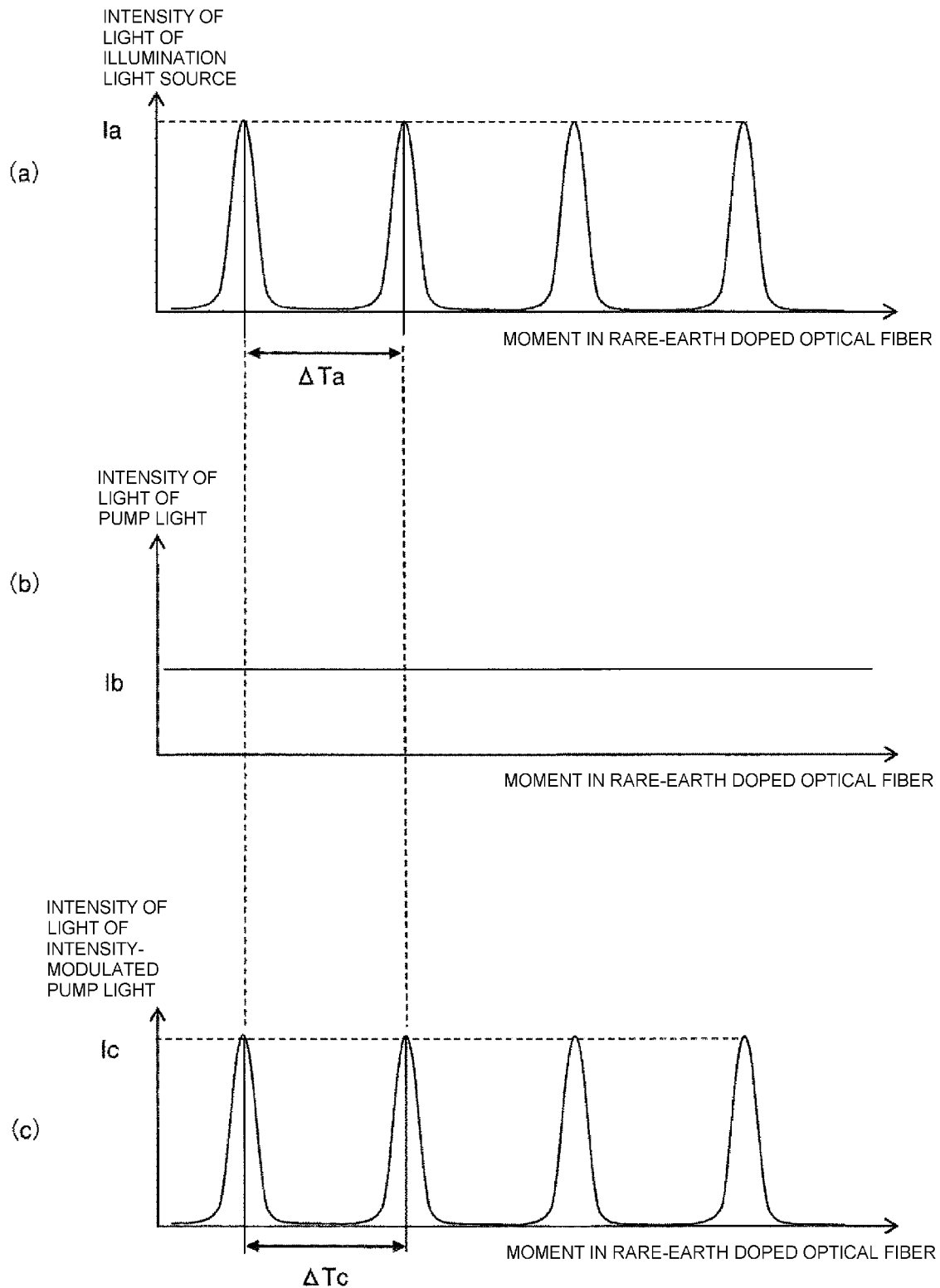

[FIG. 11]
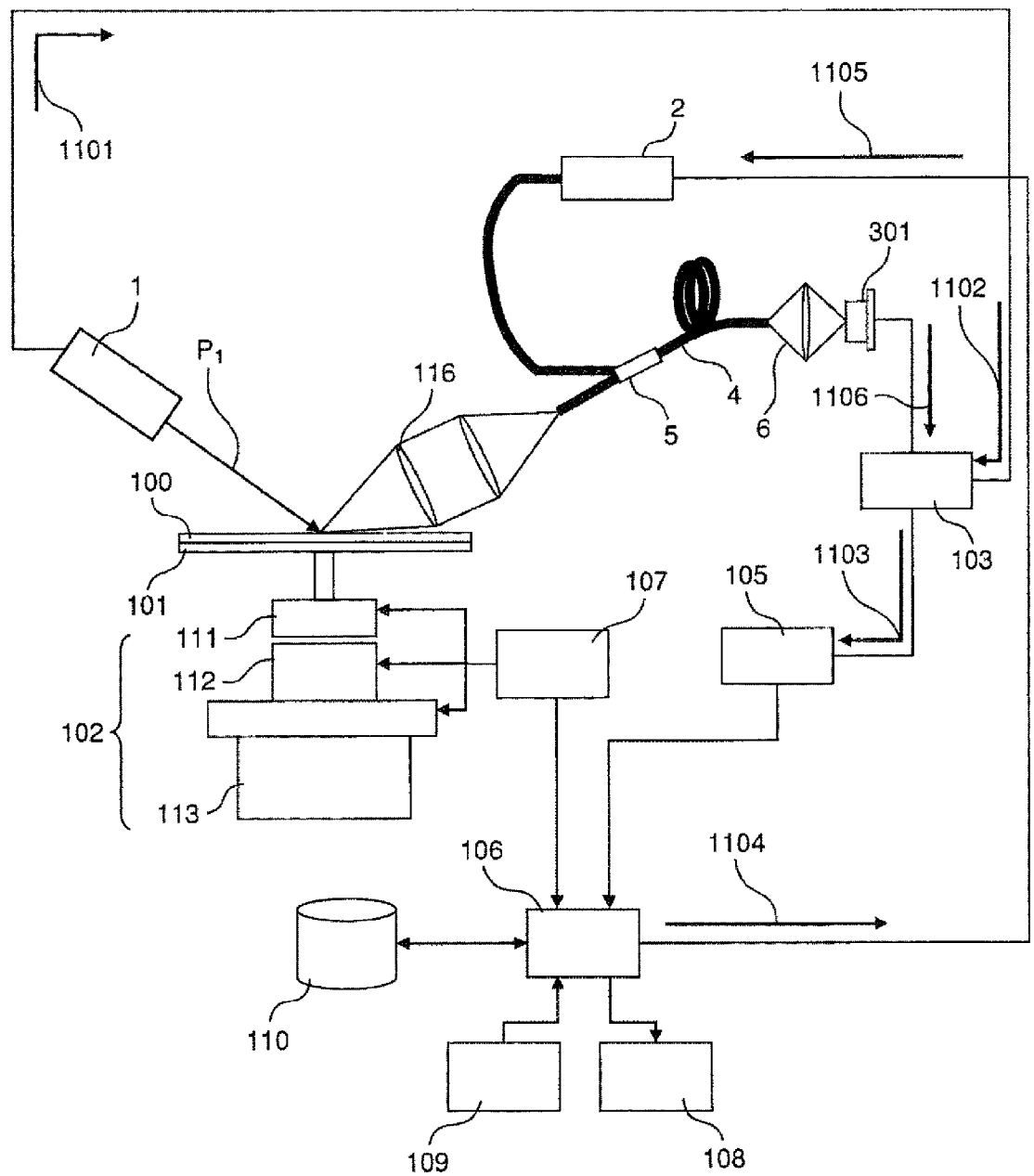

[FIG. 12]
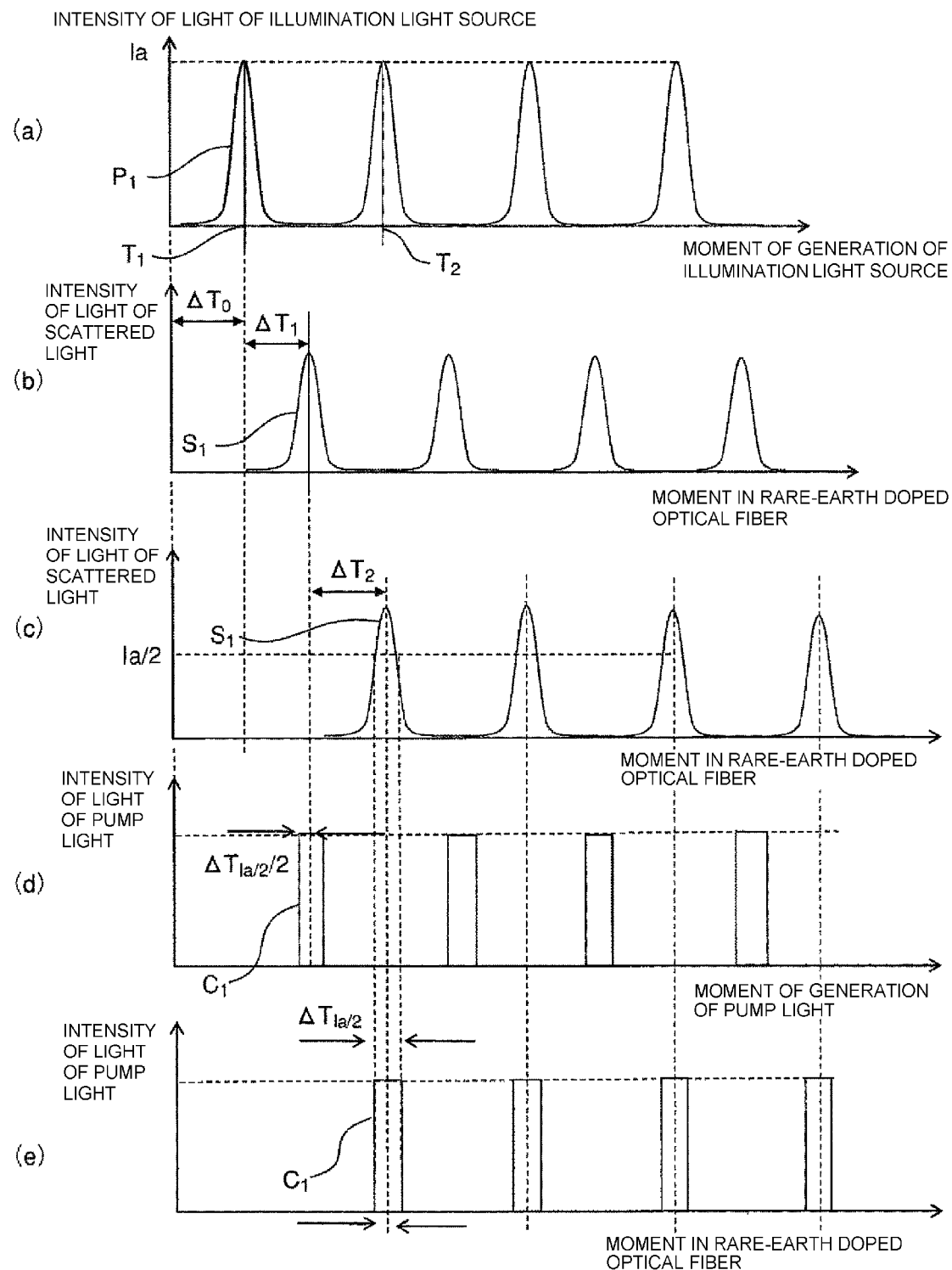

INSPECTION APPARATUS

RELATED APPLICATIONS

This application is the U.S. National Phase under 35 U.S.C. §371 of International Application No. PCT/JP2012/069787, filed on Aug. 3, 2012, which in turn claims the benefit of Japanese Application No. 2011-169731, filed on Aug. 3, 2011, the disclosures of which Applications are incorporated by reference herein.

TECHNICAL FIELD

The present invention relates to an inspection apparatus that detects a so-called defect such as a scratch and a foreign matter on a substrate, and an inspection method. The present invention relates to a surface foreign matter inspection apparatus that detects, for example, a fine defect on a so-called bare wafer, and a surface inspection method.

BACKGROUND ART

In production lines for semiconductor substrates, thin film substrates, and the like, inspections of defects that are present on surfaces of the semiconductor substrates, the thin film substrates, and the like are performed so as to maintain and improve the product yield rate. PTL 1 discloses such a surface inspection apparatus in which a sample surface is irradiated with collected illumination light and light which is scattered due to surface roughness and the defect is detected. PTL 2 discloses another inspection apparatus. PTL 3 discloses yet another technique.

CITATION LIST

Patent Literature

[PTL 1] JP-A-2005-3447
[PTL 2] JP-A-2010-99095
[PTL 3] JP-A-11-251663

SUMMARY OF INVENTION

Technical Problem

Light that is scattered by a defect on a wafer is very weak, and a photomultiplier tube (PMT) and a multi-pixel photon counter (MPPC) are used as detection methods for measuring the weak light with high speed and sensitivity. The above-described detection methods have a function of photoelectronically converting the weak light and multiplying an electron, but have a problem in that a signal light is lost and a signal-to-noise (S/N) ratio is reduced because the quantum efficiency of the photoelectron conversion is as low as 50% or less.

Solution to Problem

The present invention focuses on an optical amplification in which direct light is amplified prior to the photoelectron conversion. The optical amplification is an amplification method in which the signal light and light of pump light are introduced into a rare-earth doped fiber, a stimulated emission is caused, and the signal light is amplified. In the present invention, the optical amplification is used.

Also, in the present invention, the amplification factor is changed according to various conditions.

Advantageous Effects of Invention

According to the present invention, the inspection can be performed with a high S/N ratio.

BRIEF DESCRIPTION OF DRAWINGS

FIG. 1 is a schematic view of an inspection apparatus according to Embodiment 1.
FIG. 2 is a layout view of a detection optical system.
FIG. 3 is a diagram about an S/N ratio and an inspection position according to Embodiment 3.
FIG. 4 is a schematic view of an inspection apparatus according to Embodiment 4.
FIG. 5 is an example of an enlarged view of a detection optical system according to Embodiment 4.
FIG. 6 is another example of an enlarged view of a detection optical system according to Embodiment 5.
FIG. 7 is an example of an overall fiber view according to Embodiment 6.
FIG. 8 is a schematic view of an inspection apparatus according to Embodiment 7.
FIG. 9 is a schematic view of an inspection apparatus according to Embodiment 8.
FIG. 10 is a schematic diagram illustrating a synchronization adjustment in Embodiment 8.
FIG. 11 is a schematic view of an inspection apparatus of Embodiment 9.
FIG. 12 is a diagram illustrating a synchronization adjustment in Embodiment 9.

DESCRIPTION OF EMBODIMENTS

Hereinafter, embodiments of the present invention will be described referring to the accompanying drawings.

Embodiment 1

FIG. 1 is a schematic view of an inspection apparatus according to Embodiment 1 that includes, as shown in FIG. 1, an illumination light source 1, a stage 101, a pump light 2 that optically amplifies scattered light, an interference filter 7, a rare-earth doped optical fiber 4, a detector 3 that detects the amplified light, and a signal processing unit 105. A stage driving unit 102 has a rotary driving unit 111 that rotates the stage 101 about an axis of rotation, a vertical driving unit 112 that moves in a vertical direction, and a slide driving unit 113 that moves a sample in a radial direction. Also, as control units, an overall control unit 106 and a mechanical control unit 107 that perform various controls, which will be described later, are provided. In addition, an information display unit 108, an input operation unit 109, a storage unit 110 that stores various pieces of information and the like are provided.

The stage 101 supports a sample 100 such as a wafer. The stage 101 is horizontally moved by the slide driving unit 113 while being rotated by the rotary driving unit 111 so that illumination light relatively scans the sample 100 in a spiral shape. Accordingly, the light that is scattered by an unevenness of a sample surface is continuously generated, and the scattered light caused by defects is generated in a pulsed manner. In a surface inspection apparatus that detects the defect on the wafer, a shot noise of the light that is continuously generated is a noise component. In this embodiment, rotation and translation stages are used in the description, but a two-axis translation stage may be used.

The optical amplification in this embodiment will be described. The sample 100 is irradiated with the light from the illumination light source 1 the light that is scattered, diffracted, or reflected by the defect that is present on the sample surface or in an inner portion in the vicinity of the surface and on the sample surface is collected by a detection optical system 116 to be introduced into the rare-earth doped optical fiber 4.

The pump light 2 generates light whose wavelength is shorter than that of light generated by the illumination light source 1. When the light of the pump light 2 is incident on the rare-earth doped optical fiber 4 via a fiber coupler 5, an electronic state of a rare-earth ion that is added is excited from a ground state to an excited state and a population inversion state is formed. When a signal light is incident in this case, the rare-earth ion in the excited state causes a stimulated emission and the signal light is amplified. Then, the amplified light is incident on the detector 3 that performs a photoelectron conversion by a coupling optical system 6. In general, a photodetector performs detection through electron amplification after a photoelectron conversion. However, such a method has problems in that quantum efficiency on a photoelectron conversion surface is low and a weak current prior to the electrical amplification using a preamplifier or the like is likely to be subject to an effect caused by an electric field and a magnetic field. In contrast, the optical amplification in this embodiment has an advantage of being free from such problems because direct light is amplified before a photoelectron conversion is performed.

In a case where the illumination light source 1 is a continuous oscillation laser, a continuous emission lamp and diode laser are suitable for the pump light 2 because of they are inexpensive. When the lamp is used as the pump light 2, a band-pass filter such as the interference filter 7 may be used to take a wavelength suitable for an excitation of a rare earth. Using the diode laser, there are advantages of stability and a long service life.

Next, an optical relationship between an illumination optical system, the detection optical system, and the rare-earth doped optical fiber will be described referring to FIG. 2.

In this embodiment, the light from illumination light 201 forms an elongated and elliptically shaped illumination spot 202 on the sample 100. The detection optical system 116 that has an optical element such as a lens is arranged to have an azimuth φ of 90° with respect to a longitudinal direction of the illumination spot 202 as shown in FIG. 2(*a*) and to have an angle of elevation of χ with respect to the sample 100 as shown in FIG. 2(*b*). Herein, assuming that a diameter of the illumination spot 202 is R (in this embodiment, a length of a long axis is R), a numerical aperture of the rare-earth doped optical fiber is NA', and a core diameter of the rare-earth doped optical fiber is R', it is preferable that NA of the detection optical system 116 substantially satisfy the following relationship.

[Formula 1]

$$NA = \frac{NA' \times R'}{R}$$ (Formula 1)

In this embodiment, a plurality of the detection optical systems may be arranged as shown with a detection optical system 117 in FIG. 2(*a*). In other words, in this embodiment, the number of sensors is not limited as shown in FIG. 2(*a*), and two or more detection optical systems may be arranged such that at least ones of the azimuths φ from the illumination spot 202 and the angles of elevation χ are different from each other. The azimuth and the angle of elevation at which the scattered light from the defect is scattered vary depending on the type and property of the defect, and thus this allows a high-sensitivity detection of the various defects. The illumination spot 202 may have an elliptical shape as shown in the drawing or may have a circular shape.

The light that is amplified in this manner is imaged in the detector 3 through a lens 6 of FIG. 1. A detection result of the detector 3 is sent to the signal processing unit 105 and is compared with a threshold. A detection result that exceeds the threshold is determined to be a defect. The defect that is determined in the signal processing unit 105 is associated with a coordinate on the sample in the sample 100 and is transmitted to the overall control unit 106 and, in addition, is accommodated in the storage unit 110. Information with respect to the defect that is accommodated in the storage unit 110 is appropriately read and is displayed in the information display unit 108 in a form which is easy for an operator to view.

As above, with the inspection apparatus of this embodiment, an inspection can be performed with an S/N ratio higher than in the related art.

Embodiment 2

Next, Embodiment 2 will be described referring to FIGS. 1, 2, and 3. The description of Embodiment 2 will focus on differences thereof from Embodiment 1. This embodiment is a method for further increasing the S/N ratio during the detection of the defect.

As described above, the azimuth and the angle of elevation at which the scattered light from the defect is scattered vary depending on the type and property of the defect. Also, there is a case where the size of the scattered light from the unevenness of the sample surface is varied by a detection direction with respect to an incidence direction of the light from the illumination light source. In other words, the S/N ratio during the detection of the defect changes in association with the defect to be detected, the illumination direction, the detection direction, and the like.

In this embodiment, the plurality of detection optical systems 116 and 117, the rare-earth doped optical fibers 4 and 206 corresponding thereto, and the detector corresponding thereto are provided as shown in FIG. 2(*a*), and the detection result thereof is added. More specifically, the addition method is a weighted addition for further increasing (for example, maximizing) the total S/N ratio. In addition, in this embodiment, each of the plurality of detection optical systems 116 and 117 is provided with the pump light 2 of FIG. 1 and the intensity of the light of the pump light 2 is changed during the weighted addition so that an amplification factor of each of the detection optical systems 116 and 117 is changed and the weighting is optically performed. In this manner, the S/N ratio can be further increased when the defect is further detected.

Embodiment 3

Next, Embodiment 3 will be described referring to FIG. 3. FIG. 3(*a*) is a diagram showing a relationship between the S/N ratio and an inspection position of the sample 100. There is a case where the S/N ratio varies depending on a surface state of the substrate. Also, in a case where the number of rotations at which the sample is rotated is fixed, the time of the optical irradiation differs in a central portion and an outer circumferential portion of the sample 100, and thus the S/N ratio depends on the inspection position (in particular, the radius r from the center of the sample). As such, it is preferable that the amplification factor vary depending on the inspection position. In this embodiment, the amplification factor of the optical amplification varies depending on the inspection position (for example, the radius r from the center of the sample).

This embodiment will be described more specifically. In a case where the number of rotations of the stage 101 of FIG. 1 is fixed, the time of the optical irradiation differs in the central portion and the outer circumferential portion of the sample 100, and thus the S/N ratio depends on the inspection position. Herein, assuming the scattered light caused by surface roughness is N, a shot noise thereof is
$\sqrt{N}$
and thus the S/N ratio of the inspection apparatus is expressed as

[Formula 2]

$$S/N \text{ ratio of inspection apparatus} = \frac{S}{\sqrt{N}} \qquad \text{(Formula 2)}$$

In addition, the time of the irradiation in a unit area is in proportion to the radius r, and thus the S/N ratio is expressed as

[Formula 3]

$$S/N \text{ ratio of inspection apparatus} \propto \frac{S \times r}{\sqrt{N \times r}} = \frac{S}{\sqrt{N}} \sqrt{r} \qquad \text{(Formula 3)}$$

and is changed as shown in FIG. 3(a).

In this embodiment, the intensity of the light of the pump light 2 is changed to render the S/N ratio uniform, and the amplification factor of the optical amplification is changed depending on
$\sqrt{r}$
as shown in FIG. 3(b). In this manner, the S/N ratio can be further increased than in the related art, and sensitivity variations depending on the inspection position can be removed.

Embodiment 4

Next, Embodiment 4 will be described. This embodiment is characterized mainly by using an inclined rare-earth doped optical fiber bundle whose end surface is inclined.

FIG. 4 is a schematic view of this embodiment. In this embodiment, a wide area on the sample 100 is irradiated with the illumination light source 1 so as to shorten the time of the inspection, and the inspection is performed by using a detector with a plurality of pixels.

The light that is generated from the sample (including reflected light, diffracted light, scattered light, and the like) is collected by the detection optical system 116, and is imaged on a surface of an inclined rare-earth doped optical fiber bundle 505 whose end surface is obliquely cut and polished. The light that is imaged is introduced into a fiber bundle. Herein, the fiber bundle means a plurality of fibers that are bundled.

The light of pump light 502 is reflected by a dichroic mirror 501 in the middle of the detection optical system 116 (for example, between two lenses), and is introduced into the inclined rare-earth doped optical fiber bundle 505. The light that is amplified in the inclined rare-earth doped optical fiber bundle 505 is detected by a plural pixel detector 507.

In this case, a micro lens 506 may be used so that the light can be introduced with high efficiency. Also, each of the fibers may be arranged to correspond to each of the pixels of the plural pixel detector 507. The light of the plurality of fibers may be introduced into one of the pixels of the plural pixel detector 507.

Next, an advantage of using the inclined rare-earth doped optical fiber bundle 505 will be described.

FIG. 5(a) is a view showing an object surface 508 and an image surface 509 in a case where the scattered light is detected obliquely with respect to the sample 100. During the oblique detection, the image surface 509 is inclined by the same amount as the inclination (detected angle of elevation) $\chi$ of the object surface 508. In other words, blur occurs at both ends of the image surface. In contrast, in this embodiment, the inclined rare-earth doped optical fiber bundle 505 that is cut and polished with, for example, the inclination $\chi$ to match the inclination $\chi$ of the image surface 509 is arranged as shown in FIG. 5(b). In this manner, each light on an imaging surface can be accurately collected while the inclination of the object surface 508 is removed. In addition, a rare-earth doped optical fiber bundle 510 in which each fiber is arranged in a stair shape to match the inclination $\chi$ may be used instead of the inclined rare-earth doped optical fiber bundle 505 as shown in FIG. 5(c). In other words, the shape of a fiber bundle end surface not to be subject to an effect caused by the inclination of the object surface 508 may not be strictly inclined and a substantially inclined surface may be formed.

Embodiment 5

Next, Embodiment 5 will be described. In Embodiment 5, a rare-earth doped optical fiber bundle whose cross section is vertically cut is used to achieve the same effect as Embodiment 4.

FIG. 6 is a schematic view of a case where a rare-earth doped optical fiber bundle 602 that is vertically cut is disposed. In FIG. 6(a), the oblique detection is performed at the detected angle of elevation $\chi$ with respect to the object surface 508 as in the case of Embodiment 4. In FIG. 6(a), a micro mirror 603 is arranged obliquely with respect to an inclined axis 6000 of the detection optical system 116 on the imaging surface that is formed by the detection optical system 116. A reflection film and glass are alternately deposited in the micro mirror 603, and each light on an image surface thereof is reflected by the reflection film of the micro mirror 603. A micro lens 6031 is present on an emission side of the micro mirror 603, and the light is efficiently coupled with the rare-earth doped optical fiber bundle 602 by the micro lens 6031. The micro lens can make a sufficient end surface by photolithography.

In FIG. 6(b), a micro prism 604 is arranged on the imaging surface that can be formed by the detection optical system 116, and this also has the micro lens 6031 on an emission surface. Each light on the image surface is reflected by the micro prism 604, and is coupled with the rare-earth doped optical fiber bundle 602 by the micro lens 6031.

Assuming NA of the detection optical system, NA' as the numerical aperture of the rare-earth doped optical fiber, R' as the core diameter of the rare-earth doped optical fiber, and n as the number of pixels, the size d per pixel on the sample 100 is expressed as

[Formula 4]

$$d = \frac{NA' \times R'}{NA} \frac{1}{n} \quad \text{(Formula 4)}$$

Embodiment 6

Next, Embodiment 6 will be described. In Embodiment 6, the amplification factor in Embodiment 4 is controlled in further detail.

With regard to Embodiment 4, there is a possibility that an optical path difference ΔL is generated by the inclination of the inclined rare-earth doped optical fiber bundle 505 and the amplification factor is slightly different. However, when compared to the length of the fiber, ΔL is sufficiently small, and the difference in the amplification factor can be neglected. However, it is preferable that there be no difference in the amplification factor.

In this embodiment, an adjusted rare-earth doped optical fiber bundle 704 in which the total length of each fiber is adjusted to offset an effect caused by the optical path difference ΔL is used as shown in FIG. 7. More specifically, each light on the image surface 509 is incident on the adjusted rare-earth doped optical fiber bundle 704 that is fixed by a fixing tool 702. Herein, the length of a fiber 7031 is adjusted to a length at which the effect caused by the optical path difference ΔL is removed. As such, the light that passes through the fiber 7031 is not subject to the effect caused by the optical path difference ΔL. This is the same with regard to other fibers 7032 to 7035. In other words, the fibers 7031 to 7035 have the length at which the effect caused by the optical path difference ΔL is removed, and the length of each can be expressed to be different from the others. End surfaces of the fibers 7031 to 7035 are aligned by a fixing unit 701 such that there is no optical path difference. The emitted light that is emitted is detected by the plural pixel detector 507 via the micro lens 506.

Herein, a multi-channel PMT with a small dark current, a CCD, an electron multiplying CCD (EMCCD), and an electron bombardment CCD (EB-CCD) with a high pixel number are suitable as the detector with the plurality of pixels.

Herein, in a case where the multi-channel PMT in which the size per pixel of the detector is larger when compared to a CCD camera or the like is used, there is a case where a magnifying optical system with a magnification factor of at least ten is required and a large space is required. In addition, in a case where the magnifying optical system is required, the detection optical system approaches the sample 100, and thus there is a case where a numerical aperture of a detection lens cannot be sufficient depending on the angle of elevation χ. According to this embodiment, the light of each fiber can be introduced to a corresponding channel with a free gap at the fiber bundle end even in a case where the detector whose size per pixel is large is used, and there is an advantage that a special optical system such as the magnifying optical system is not required.

Embodiment 7

Next, Embodiment 7 will be described. In a case where the above-described illumination light source 1 and pump light 2 are a pulse oscillation laser, there is a case where natural radiation caused by the light of the pump light 2 occurs to become a noise for which a desired S/N ratio is not obtained if the light (reflected light, diffracted light, scattered light, and the like) caused by the radiation of the illumination light source 1 and the light of the pump light 2 are not temporally synchronized in the rare-earth doped optical fiber. With this embodiment, the problem is solved. This embodiment is characterized by including a synchronization unit that temporally synchronizes the scattered light caused by the radiation of the illumination light source 1 with the light of the pump light 2 in the rare-earth doped optical fiber.

FIG. 8 is a view illustrating this embodiment. The sample 100 is irradiated with pulsed light from the illumination light source 1 (in this embodiment, a pulse oscillation laser light source). The light (reflected light, diffracted light, scattered light, and the like) caused by the radiation of the illumination light source 1 is collected by the detection optical system 116 that has the lens or the like. The light that is collected is incident on the rare-earth doped optical fiber 4. In contrast, the pulsed light from the pump light 2 (in this embodiment, the pulse oscillation laser light source) is reflected by a mirror 802 and then is incident on a synchronization unit 808. The synchronization unit 808 has, for example, two mirrors 803 and 804 and a driving mechanism 810 such as a stage that changes positions (may be referred to as optical path lengths) thereof. In the synchronization unit 808, the mirrors 803 and 804 can be moved as shown with an arrow 806, and an optical distance of the pulsed light from the pump light 2 can be changed. The pulsed light that passes through a path whose optical distance is changed is reflected by a mirror 805 and is incident on the rare-earth doped optical fiber 4. By changing the optical distance of the pulsed light from the pump light 2 in this manner, the moment when the pulsed light from the pump light 2 is incident on the rare-earth doped optical fiber 4 can be changed. In other words, the light (reflected light, diffracted light, scattered light, and the like) caused by the radiation of the illumination light source 1 and the light of the pump light 2 can be synchronized when incident on the rare-earth doped optical fiber.

During the inspection, the synchronization can be sufficiently achieved by obtaining a time difference between when the light (reflected light, diffracted light, scattered light, and the like) caused by the radiation of the illumination light source 1 and the light of the pump light 2 are incident on the rare-earth doped optical fiber in advance.

In this embodiment, oscillation frequencies may be different, but emission in the same oscillation period is preferable for the S/N ratio. Also, the light may be guided simultaneously in the fibers by electrically delaying an oscillation of any one of the fibers without using the stage for optical path length adjustment.

Embodiment 8

Next, Embodiment 8 will be described. This embodiment is characterized by the illumination light source 1 being the pulse oscillation laser light source and the pump light 2 being a continuous emission light source, and further including an optical intensity modulator 901 that intensity-modulates light of an excitation light source.

FIG. 9 is a view illustrating this embodiment. This embodiment has the same configuration as Embodiment 7 except that the illumination light source 1 is the pulse oscillation laser light source and the pump light 2 is the continuous emission light source, and this embodiment further includes the optical intensity modulator 901 that optically intensity-modulates the light of the excitation light source.

FIG. 10 is a diagram illustrating a timing adjustment at a time when the optical intensity of the pump light 2 is adjusted by using the optical intensity modulator. The illumination light source 1 emits pulsed light that has a Gaussian profile with a time interval ΔTa and a peak intensity Ia as shown in FIG. 10(*a*). On the other hand, the pump light 2 is the continuous emission light source, and emits continuous oscillation light that has a fixed intensity Ib at any moment as shown in FIG. 10(*b*). In this embodiment, the optical intensity modulator 901 converts the waveform shown in FIG. 10(*b*) to the waveform shown in FIG. 10(*c*). More specifically, the optical intensity modulator 901 converts a waveform of the pump light 2 to continuous pulsed light, converts the intensity Ib to an intensity Ic (preferably, an intensity at which the stimulated emission of the rare-earth ion is performed efficiently), and causes the moments of generation of the peak intensity in the rare-earth doped optical fiber to coincide with each other. In addition, the time interval is ΔTc (=ΔTa). In this manner, the temporal synchronization in the rare-earth doped optical fiber can be achieved even in a case where the illumination light source 1 is the pulse oscillation laser light source and the pump light 2 is the continuous emission light source. A chopper may be used as a modulator.

Embodiment 9

Next, Embodiment 9 will be described. This embodiment is characterized by the illumination light source 1 being the pulse oscillation laser light source and the pump light 2 being the continuous emission light source, and further including a processing unit that electrically synchronizes at least one of the moment and time of generation of the continuous oscillation light of the pump light 2 with at least one of the moment and time of generation of a pulse signal of the illumination light source 1, and an MPPC that is an example of a detector which is capable of high-speed response. Except for this, this embodiment has the same configuration as Embodiment 1. This embodiment is particularly effective in a case where a detector (for example, the MPPC) that is capable of relatively higher-speed response compared to other detectors is used.

This embodiment will be described referring to FIG. 11, and the same description as in the other embodiments will be omitted. When pulsed light $P_1$ is emitted from the illumination light source 1, a generation timing signal showing a moment of generation $T_1$ thereof is sent from the illumination light source 1 to a synchronization unit 103 (arrows 1101 and 1102). Herein, in the synchronization unit 103, a detection timing signal showing a moment of detection of the pulsed light $P_1$ by an MPPC 301 can also be detected (arrow 1106). $T_1$ that is detected in the synchronization unit 103 is sent to the signal processing unit 105 (arrow 1103) with a delay signal and a continuation signal which can be arbitrarily changed. In the signal processing unit 105, $T_1$, the delay signal, and the continuation signal are used to perform a calculation so that a moment and time of synchronization between excitation light from the pump light 2 and the scattered light from the sample 100 in the rare-earth doped optical fiber 4 are obtained. The moment and the time that are calculated in the signal processing unit 105 are transmitted to the pump light 2 (arrows 1104 and 1105) through the overall control unit 106. Then, the pump light 2 oscillates the continuous oscillation light at the moment and time calculated in the signal processing unit 105.

A further detailed description of this embodiment will be made referring to FIG. 12. FIG. 12 is a diagram illustrating timings at which the pulsed light from the illumination light source 1 and the light from the pump light 2 of this embodiment are generated. In this embodiment, the time of generation of the continuous oscillation light from the pump light is the full width at half maximum of the pulsed light from the illumination light source 1.

As shown in FIG. 12(*a*), the pulsed light $P_1$ from the illumination light source 2 is expressed as a Gaussian profile with the peak intensity Ia and the moment of generation $T_1$. As shown in FIG. 12(*b*), scattered light $S_1$ that is generated from the sample 100 by the illumination of $P_1$ is guided to the rare-earth doped optical fiber 4 with a delay of the amount of $\Delta T_1$ from $T_1$. Herein, as shown in FIG. 12(*c*), $S_1$ is further guided by the amount of $\Delta T_2$ while the light from the pump light 2 is guided to the rare-earth doped optical fiber 4. In this embodiment, as shown in FIG. 12(*d*), continuous oscillation light $C_1$ is generated from the pump light 2 at a moment which is the half width at half maximum $\Delta T_{Ia/2}/2$ of $P_1$ earlier than the moment $T_1+\Delta T_1$. In other words, the moment when the continuous oscillation light $C_1$ is generated is $T_1+\Delta T_1-\Delta T_{Ia/2}/2$. In this manner, as shown in FIG. 12(*e*), $C_1$ can be synchronized with $S_1$ in a rare-earth fiber. More specifically, the center of the profile of $C_1$ matches the moment of guiding of the peak intensity of $S_1$, and the time of generation of $C_1$ is the full width at half maximum $\Delta T_{Ia/2}$ of the pulsed light from the illumination light source 1. These calculations are performed by the synchronization unit 103 and the signal processing unit 105, and $\Delta T_1$, $\Delta T_2$, and the like are the above-described delay time and the full width at half maximum $\Delta T_{Ia/2}$ is the continuation time.

Waveforms of $P_1$, $S_1$, and $C_1$ described above can be sufficiently obtained by an optical simulation, a prior actual measurement using a photoelectron conversion element such as a photodiode, and the like.

The moment and time of generation of $C_1$ can be arbitrarily changed, and the full width at half maximum can be the full width at half maximum of the scattered light $S_1$.

In the above description of Embodiments 1 to 9, a semiconductor wafer is used as the sample. However, an inspection target of the inspection method and the inspection apparatus is not limited to the semiconductor wafer. The inspection target can also be applied to an inspection of substrates of a hard disk, a liquid crystal panel, a solar power panel, and the like.

REFERENCE SIGNS LIST

1 Illumination light source
2, 502 Pump light
3 Detector
4, 206 Rare-earth doped optical fiber
5 Fiber coupler
6 Coupling optical system
7 Interference filter
100 Sample
101 Stage
102 Stage driving unit
103 Synchronization unit
105 Signal processing unit
106 Overall control unit
107 Mechanical control unit
108 Information display unit
109 Input operation unit
110 Storage unit
111 Rotary driving unit
112 Vertical driving unit
113 Slide driving unit
116 Detection optical system 201 Illumination light
202 Illumination spot
301 MPPC
501 Dichroic mirror
505 Inclined rare-earth doped optical fiber bundle
506 Micro lens
507 Plural pixel detector
508 Object surface
509 Image surface
510 Step-shaped rare-earth doped optical fiber bundle
602 Rare-earth doped optical fiber bundle
603 Micro mirror
604 Micro prism
701 Fixing unit
704 Adjusted rare-earth doped optical fiber bundle
7031 Fiber

The invention claimed is:

1. An inspection apparatus that detects a defect of a substrate, comprising:
   an illumination optical system that irradiates the substrate with an illumination light;
   a first detection optical system that detects a light from the substrate;
   a first optical amplification optical system that optically amplifies the light which is detected by the first detection optical system, the light being optically amplified by a stimulated
   emission by an optical fiber;
   a first excitation optical system that includes the optical fiber that generates a first excitation light for the optical amplification;
   a first photoelectron conversion system that photoelectronically converts the light which is amplified by the optical amplification optical system into an electric signal; and
   a processing unit that detects the defect by using the electric signal from the first photoelectron conversion system, wherein:
   a wavelength of the excitation light is shorter than a wavelength of the illumination light and
   a numerical aperture NA of the first detection optical system, a numerical aperture NA' of the optical fiber, a diameter R of a spot of the illumination light, and a core diameter R' of the
   optical fiber satisfy the following relation:

$NA = (NA' \times R')/R.$

2. The inspection apparatus according to claim 1, further comprising:
   a second detection optical system that detects the light from the substrate;
   a second optical amplification optical system that optically amplifies the light which is detected by the second detection optical system;
   a second excitation optical system that generates a second excitation light for the optical amplification by the second optical amplification optical system;
   a second photoelectron conversion system that photoelectronically converts the light which is amplified by the second optical amplification optical system into an electric signal; and
   a control unit that changes at least one of an intensity of the first excitation light and an intensity of the second excitation light,
   wherein the processing unit performs a weighted addition by using the electric signal from the first photoelectron conversion system and the electric signal from the second photoelectron conversion system.

3. The inspection apparatus according to claim 1, further comprising a control unit that changes an intensity of the first excitation light according to a position of the substrate.

4. The inspection apparatus according to claim 1, wherein:
   the first detection optical system is an oblique detection optical system,
   the optical fiber of the first optical amplification optical system is a rare-earth doped optical fiber bundle in which a plurality of rare-earth doped optical fibers are bundled, and
   a surface of the rare-earth doped optical fiber bundle that detects the light which is detected by the first detection optical system is inclined.

5. The inspection apparatus according to claim 1,
   wherein the first detection optical system is an oblique detection optical system, and
   a micro mirror and a micro lens are provided between the first detection optical system and the first optical amplification optical system.

6. The inspection apparatus according to claim 1,
   wherein the first detection optical system is an oblique detection optical system, and
   a micro prism and a micro lens are provided between the first detection optical system and the first optical amplification optical system.

7. The inspection apparatus according to claim 1,
   wherein the first detection optical system is an oblique detection optical system,
   the optical fiber of the first optical amplification optical system is a rare-earth doped optical fiber bundle in which a plurality of rare-earth doped optical fibers are bundled, and
   the plurality of rare-earth doped optical fibers have different lengths.

8. The inspection apparatus according to claim 1, further comprising
   a synchronization unit that temporally synchronizes the light from the substrate with the first excitation light in the first optical amplification optical system.

* * * * *